US00PP34987P2

(12) United States Plant Patent
Hartman

(10) Patent No.: US PP34,987 P2
(45) Date of Patent: Feb. 14, 2023

(54) ***CALADIUM* PLANT NAMED 'WON OF14-1246'**

(50) Latin Name: ***Caladium* X *hortulanum***
Varietal Denomination: 'WON OF14-1246'

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 17/894,085

(22) Filed: Aug. 23, 2022

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 6/10
See application file for complete search history.

*Primary Examiner* — Anne Marie Grunberg
(74) *Attorney, Agent, or Firm* — C. Anne Whealy

(57) ABSTRACT

A new and distinct cultivar of *Caladium* plant named 'WON OF14-1246', characterized by its compact, relatively short to intermediate in height; upright to somewhat mounding plant habit; dense, leafy and bushy appearance; vigorous growth habit and rapid growth rate; lance-type leaves that are greenish white to white in color with interveinal areas that are variably flushed with red to purplish red, veins that are greyed green in color and thin dark green-colored margins and petioles that are green to greenish tan brown in color.

4 Drawing Sheets

Figure 1:
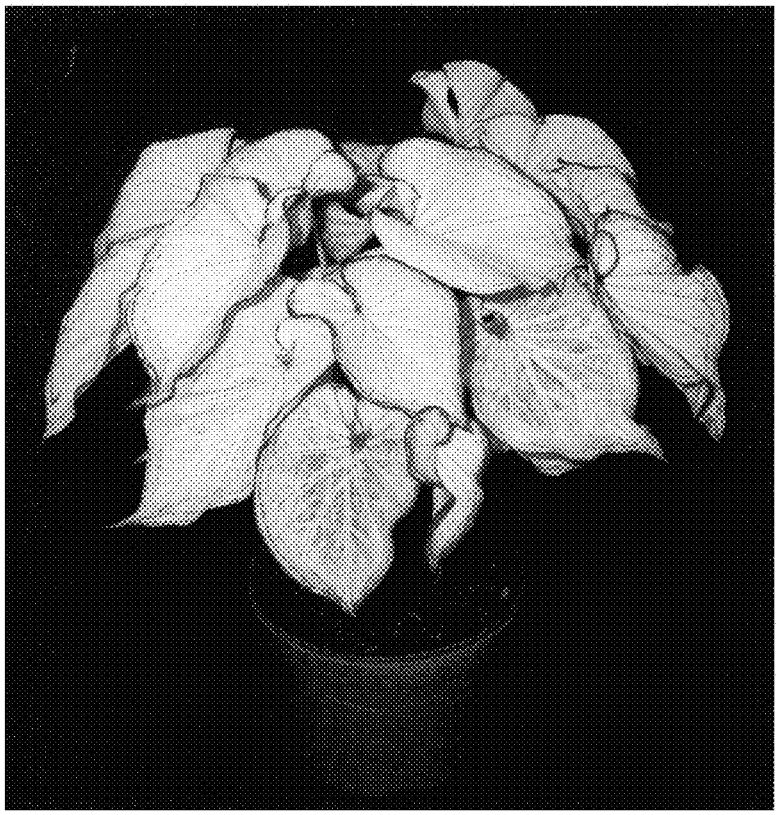

Botanical designation: *Caladium* X *hortulanum*.
Cultivar denomination: 'WON OF14-1246'.

BACKGROUND OF THE INVENTION

The present invention relates to a new and distinct cultivar of *Caladium* plant, botanically known as *Caladium* X *hortulanum*, commercially referred to as a lance leaf-type *Caladium* and hereinafter referred to by the name 'WON OF14-1246'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2013 in Avon Park, Fla. of *Caladium* X *hortulanum* 'White Wonder', disclosed in U.S. Plant Pat. No. 21,044, as the female, or seed, parent with *Caladium* X *hortulanum* 'RS-03-03', disclosed in U.S. Plant Pat. No. 26,265, as the male, or pollen, parent. The new *Caladium* plant was discovered and selected by the Inventor as a single plant within the progeny of the stated cross-pollination in a controlled outdoor nursery environment in Avon Park, Fla. in September, 2014.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2015 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'WON OF14-1246'. These characteristics in combination distinguish 'WON OF14-1246' as a new and distinct *Caladium* plant:

1. Compact, relatively short to intermediate in height; upright to somewhat mounding plant habit; dense, leafy and bushy appearance.
2. Vigorous growth habit and rapid growth rate.
3. Lance-type leaves that are greenish white to white in color with interveinal areas that are variably flushed with red to purplish red, veins that are greyed green in color and thin dark green-colored margins.
4. Petioles that are green to greenish tan brown in color.

Plants of the new *Caladium* differ primarily from plants of the female parent, 'White Wonder', in the following characteristics:

1. Plants of the new *Caladium* are more compact than plants of 'White Wonder'.
2. Leaves of plants of the new *Caladium* are greenish white to white in color with interveinal areas that are variably flushed with red to purplish red, veins that are greyed green in color and thin dark green-colored margins whereas leaves of plants of 'White Wonder' are white to grey-green in color with light pink to white-colored venation and dark green-colored borders.
3. Leaf petioles of plants of the new *Caladium* are green to greenish tan brown in color whereas leaf petioles of plants of 'White Wonder' are tannish pink in color with greenish brown-colored stripes.

Plants of the new *Caladium* differ primarily from plants of the male parent, 'RS-03-03', in the following characteristics:

1. Plants of the new *Caladium* are more compact and more mounding than plants of 'RS-03-03'.
2. Leaves of plants of the new *Caladium* are greenish white to white in color with interveinal areas that are variably flushed with red to purplish red, veins that are greyed green in color and thin dark green-colored margins whereas leaves of plants of 'RS-03-03' are pearlescent white to greenish white in color with dark green-colored margins and white to greenish white-colored venation.
3. Leaf petioles of plants of the new *Caladium* are green to greenish tan brown in color whereas leaf petioles of plants of 'RS-03-03' are green to tannish green with brownish green-colored stippling.

Plants of the new *Caladium* can be compared to plants of *Caladium* X *hortulanum* 'White Delight', disclosed in U.S. Plant Pat. No. 21,216. In side-by-side comparisons, plants of the new *Caladium* differ primarily from plants of 'White Delight' in the following characteristics:

1. Leaves of plants of the new *Caladium* are greenish white to white in color with interveinal areas that are variably flushed with red to purplish red, veins that are greyed green in color and thin dark green-colored margins whereas leaves of plants of 'White Delight' are white to grey-green in color with white-colored main veins and dark green-colored borders.
2. Leaf petioles of plants of the new *Caladium* are green to greenish tan brown in color whereas leaf petioles of plants of 'White Delight' are darker greenish brown with brown- colored markings.

Plants of the new *Caladium* can also be compared to plants of *Caladium* X *hortulanum* 'White Diamond', disclosed in U.S. Plant Pat. No. 22,215. In side-by-side comparisons, plants of the new *Caladium* differ primarily from plants of 'White Diamond' in the following characteristics:

1. Leaves of plants of the new *Caladium* are greenish white to white in color with interveinal areas that are variably flushed with red to purplish red, veins that are greyed green in color and thin dark green-colored margins whereas leaves of plants of 'White Diamond' are white to grey-green in color with white-colored main veins and dark green-colored borders.
2. Leaf petioles of plants of the new *Caladium* are green to greenish tan brown in color whereas leaf petioles of plants of 'White Diamond' are green in color with dark brownish green-colored markings.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'WON OF14-1246' grown in a container that has had its tuber de-eyed prior to planting.

Figure 2:
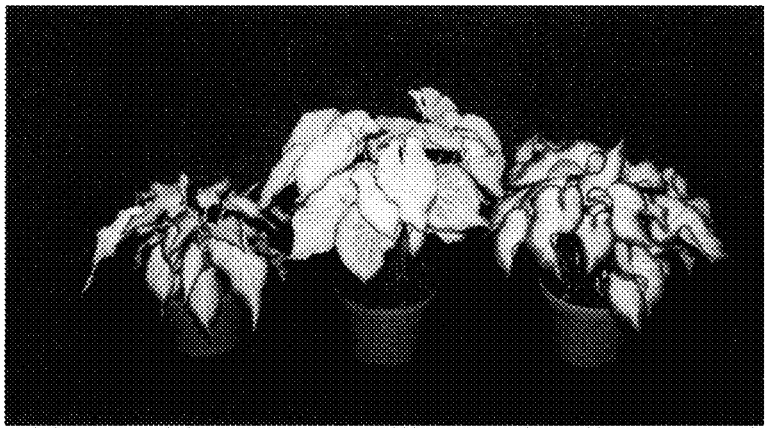

The photograph at the top of the second sheet (FIG. 2) is side perspective view of typical plants of the female parent, 'White Wonder' (right), 'WON OF14-1246' (center) and the male parent, 'RS-03-03' (left).

Figure 3:
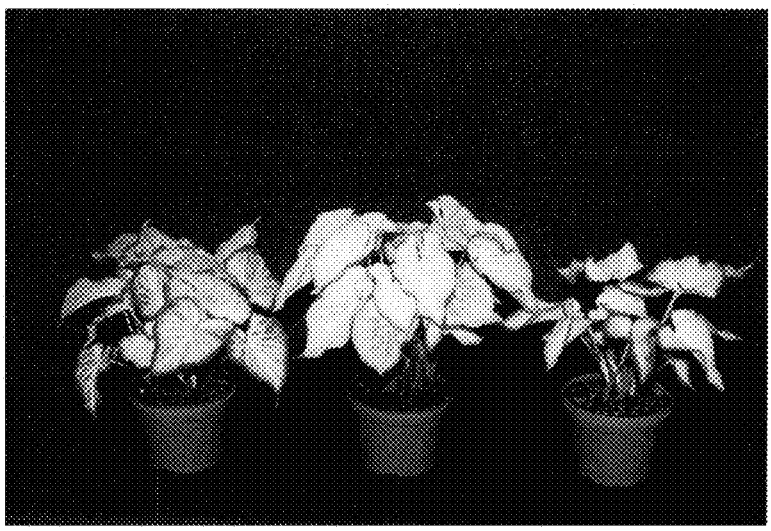

The photograph at the bottom of the second sheet (FIG. 3) is side perspective view of typical plants of 'White Delight' (right), 'WON OF14-1246' (center) and 'White Diamond' (left).

Figure 4:
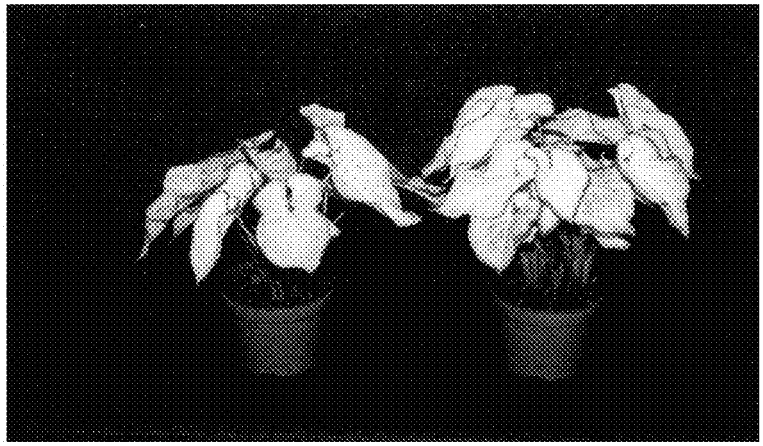

The photograph at the top of the third sheet (FIG. 4) is a comparison view of typical plants of 'WON OF14-1246' grown in containers, the plant on the left has not had its tuber de-eyed and the plant on the right has had its tuber de-eyed prior to planting.

Figure 5:
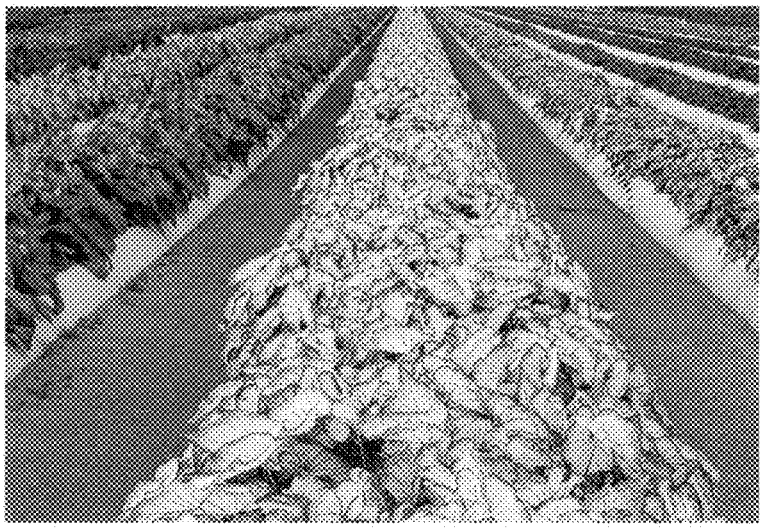

The photograph at the bottom of the third sheet (FIG. 5) is a side perspective view of typical plants of 'WON OF14-1246' grown in an open production field.

Figure 6:
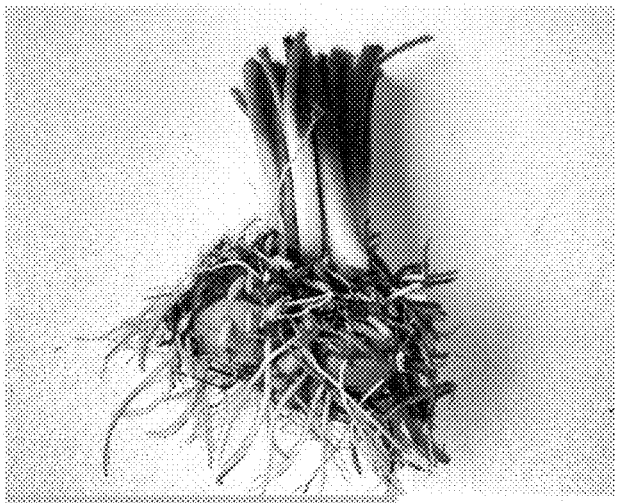

The photograph at the top of the fourth sheet (FIG. 6) is a close-up view of typical freshly-harvested tubers with roots and leaf petioles of 'WON OF14-1246'.

Figure 7:
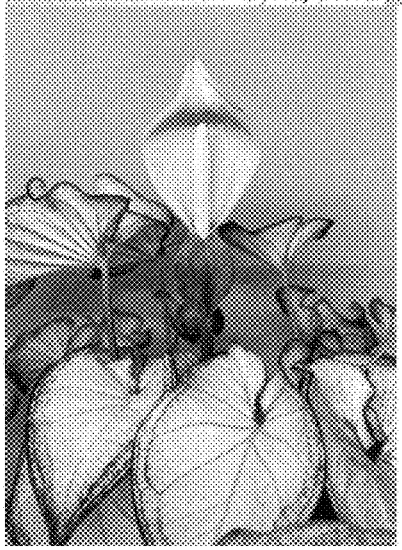

The photograph at the bottom of the fourth sheet (FIG. 7) is a close-up view of a typical flowering plant of 'WON OF14-1246'.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 1,300 μmol. During the production of the outdoor nursery-grown plants, day temperatures ranged from about 29° C. to 35° C., night temperatures ranged from about 23° C. to 26° C. and full sunlight conditions. Plants grown in the shade house were eight weeks old and plants grown in the outdoor nursery were seven months old when the photographs and the detailed description were taken. In the following description, color references are made to The Royal Horticultural Society Colour Chart, 2015 Edition, except where general terms of ordinary dictionary significance are used.

Botanical classification: *Caladium* X *hortulanum* 'WON OF14-1246'.

Parentage:

*Female, or seed, parent.*—*Caladium* X *hortulanum* 'White Wonder' disclosed in U.S. Plant Pat. No. 21,044.

*Male, or pollen, parent.*—*Caladium* X *hortulanum* 'RS-03-03', disclosed in U.S. Plant Pat. No. 26,265.

Propagation:

*Type*.—By "chipping" the tubers.

*Time to initiate roots, summer*.—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented, clumping and branched; individual segments are ovate to irregular in shape. Height: About 2.9 cm to 3.4 cm. Diameter: About 5.4 cm to 6.5 cm. Segment height: About 2.9 cm. Segment diameter: About 3.6 cm to 4.7 cm. Axillary bud shape: Roughly triangular. Axillary bud height: About 3.7 mm. Axillary bud width: About 4.7 mm. Texture: Thick, starchy; somewhat brittle. Color: Periderm, freshly-harvested: Close to 199D. Periderm, dried: Close to 200A to 200B and 199A. Epidermis: Close to 155D and 158D. Cortical tissue: Close to 8D tinged with close to 1D. Axillary buds: Close to 36C. Root description: Moderately thick, fleshy contractile roots with a moderate number of lateral branches; color, close to 155C faintly tinged with close to 182D, actual color of the roots is dependent on substrate composition, water quality, fertilizer type and formulation, substrate temperature and physiological age of roots. Rooting habit: Dense.

Plant description:

*Plant type*.—Herbaceous perennial; suitable as a potted plant in containers 15-cm to 25-cm and suitable as a landscape plant in shaded areas.

*Plant and growth habit*.—Compact, relatively short to intermediate in height; upright to somewhat mounding plant habit; dense, leafy and bushy appearance; vigorous growth habit and rapid growth rate; potted plants finish in saleable form in about eight weeks after planting tubers; leaf petioles and leaves arise from one or more growing points on tubers; leaf petioles initially upright and leaning outwardly with development.

*Plant height, from soil level to top of foliar plane, shade house-grown potted plants*.—About 21 cm to 26 cm.

*Plant height, from soil level to top of floral plane, shade house-grown potted plants*.—About 29 cm.

*Plant diameter, shade house-grown potted plants*.—About 34 cm to 39 cm.

*Number of shoots per plant, shade house-grown potted plants, tubers de-eyed*.—About five to eight develop per #1 tuber.

*Number of shoots per plant, shade house-grown potted plants, tubers not de-eyed*.—About four develop per #1 tuber.

*Cataphylls, shade house-grown potted plants*.—Length: About 3.5 cm to 5 cm. Width: About 1.2 cm to 1.4 cm. Shape: Narrowly lanceolate to linear. Apex: Acuminate. Base: Sheathing the stem. Texture and luster, outer and inner surfaces: Smooth, glabrous; semi-glossy. Color, outer surface: Close to N170D, 146D and 147A tinged with close to 199B and streaked and stippled with close to 200C and 200D; color becoming closer to 200B and 200C with subsequent development. Color, inner surface: Close to 155A tinged with close to N170D with small veins, close to 197B; colors and color patterns visible from outer surface visible.

Leaf description:

*Arrangement and type*.—Alternate; simple; lance-type.

*Length, shade house-grown potted plants*.—About 12.5 cm to 18 cm.

*Width, shade house-grown potted plants*.—About 7 to 11.5 cm; when flattened, about 8 cm to 12.5 cm.

*Shape*.—Ovate to broadly lanceolate.

*Apex*.—Acuminate.

*Base*.—Sagittate-peltate; cordate; anterior lobes often imbricate or folded inwardly.

*Margin*.—Entire; somewhat wavy with broad undulations.

*Texture and luster, upper surface*.—Smooth, glabrous; thin; dull sheen.

*Texture and luster, lower surface*.—Smooth, glabrous; slightly glaucous; dull sheen.

*Venation pattern*.—Pinnate and palmate.

*Color, shade house-grown potted plants*.—When developing, upper surface: Ground color: Close to 155B, 155C and N155D variably flushed with close to 185B, 185C and 185D. Margins: Towards the margins, close to 155B, 155C, 194D, 195D and 147A; edges, close to 147A and at the apex, close to N186C. Basal notch: Close to 187B. Midvein and lateral venation: Close to 195B with streaks, close to 191A and 147B; may be tinged or flushed with close to 187C. When developing, lower surface: Ground color: Close to 155B and 155C variably flushed with close to 185B, 185C and 185D. Margins: Towards the margins, close to 145D, 147A and 147C; at the edges, close to 147A and 147C and at the apex, close to N186C. Basal notch: Close to 187B. Midvein and lateral venation: Close to 160D with streaks, close to 137B and 137C. Fully expanded leaves, upper surface: Ground color: Close to 155C to more white than 155C and slightly and variably flushed with close to 185C and 185D. Margins: Towards the margins, close to 155C, 194D and 147A; edges, close to 147A and at the apex, close to N186C. Basal notch: Close to 187B. Midvein and lateral venation: Close to 194A and 194C with streaks, close to 147B and 147C. Fully developed leaves, lower surface: Ground color: Close to 157C and 157D. Margins: Towards the margins, close to 145D, 147A and 147C; at the edges, close to 147A and 191A and at the apex, close to N186C. Basal notch: Close to 187B. Midvein and lateral venation: Close to 147C with streaks, close to 137C.

*Petioles*.—Aspect: Initially upright and straight and leaning outwardly with development; flexible. Length, shade house-grown potted plants: About 16 cm to 22.5 cm. Diameter, distally, shade house-grown potted plants: About 2 mm to 3 mm. Diameter, proximally, shade house-grown potted plants: About 4 mm to 6 mm. Texture: Smooth, glabrous; glaucous. Color, shade house-grown potted plants: Close to 147C with stippling and streaks, close to N199A; may also be tinged or flushed with close to 199B; or close to N199A tinged with close to 147B with stippling and streaks, close to 147B; just below the leaf junction, close to N199A with stippling and streaks, close to 200C and may also be tinged with close to N170D. Wing length, shade house-grown potted plants: About 4.4 cm to 6.2 cm. Wing diameter, shade house-grown potted plants: About 6 mm to 8 mm. Texture and luster, inner and outer surfaces: Smooth, glabrous; dull sheen. Wing color, shade house-grown potted plants: Inner surface: Close to 155A tinged with close to N170D and small veins, close to 197B; colors and patterns on the outer surface are visible on the inner surface. Outer surface: Close to N170D, 146D and 147A tinged with close to 199B with stippling and streaks, close to 200C and 200D.

Inflorescence description:

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with camphor note.

*Natural flowering season and flower longevity*.—Plants of the new *Caladium* typically flower during the spring and summer in central Florida; flowers develop about nine weeks after growth commences; inflorescences last about three days before fading; inflorescences persistent.

*Spathe*.—Length, overall: About 10 cm. Length, distal open portion: About 7 cm. Length, proximal closed portion: About 3 cm. Width, distal open portion: About 4.4 cm. Depth, distal open portion: About 1.8 cm. Width, at constriction: About 1.25 cm. Width, proximal closed portion: About 2.3 cm. Shape, open portion: Elliptic. Apex: Acuminate. Base: Acute. Margin: Entire; slightly reflexed. Texture and luster, front surface: Smooth, glabrous; dull sheen. Texture and luster, rear surface: Smooth, glabrous; dull sheen; proximally, glaucous. Color, front surface: Distal open portion: Close to N155D with margins, tinged with close to 157A; with subsequent development, distally becoming closer to 199A and N199B. Proximal closed portion: Close to 147D; proximally, flushed with close to 187A; color does not change with subsequent development. Color, rear surface: Distal open portion: Close to N155D with margins, close to 157A and centers, flushed with close to 146D; color does not change with subsequent development. Proximal closed portion: Close to 147B and 147C with random and variable areas, close to 147D and 145D; color does not change with subsequent development.

*Spadix*.—Length, overall: About 6.7 cm. Length, male flower zone: About 3.4 cm. Length, sterile zone: About 1.6 cm. Length, female flower zone: About 1.7 cm. Diameter, male flower zone: About 7 mm. Diameter, sterile flower zone: About 5 mm. Diameter, female flower zone: About 8 mm. Shape: Columnar, spindle-shaped. Apex: Acute, rounded. Base: Obtuse. Aspect: Upright. Color, mature, male zone: Close to 155A tinged with close to 145D. Color, mature, sterile zone: Close to 155D. Color, mature, female zone: Close to 158B. Male flowers: Quantity per spadix: About 96. Shape: Obovate. Height: About 3 mm. Diameter: About 3 mm to 3.5 mm. Pollen amount: Moderate to abundant. Pollen color: Close to 4D. Female flowers: Quantity per spadix: About 175. Shape: Obovate. Height: About 2.8 mm. Diameter: About 1.8 mm to 2 mm. Stigma color: Close to 158B. Ovary color: Close to N170D.

*Scapes*.—Length: About 19 cm. Diameter: About 4.5 mm. Strength: Sturdy; somewhat flexible. Aspect: Mostly erect, straight. Texture and luster: Smooth, glabrous; slightly glossy and distally, glaucous; dull sheen. Color: Close to 147B faintly stippled and streaked with close to 147A and faintly tinged with close to 200A; just below spathe, close to 147B and 147D faintly stippled and streaked with close to 147A and tinged with close to 200C.

*Seeds and fruits*.—To date, seed and fruit development have not been observed on plants of the new *Caladium*.

Pathogen tolerance/resistance: Plants of the new *Caladium* have been observed to have average tolerance to *Pythium* Root Rot and average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'WON OF14-1246' as illustrated and described.

* * * * *